United States Patent [19]
Heller et al.

[11] Patent Number: 5,262,305
[45] Date of Patent: Nov. 16, 1993

[54] INTERFERANT ELIMINATING BIOSENSORS

[75] Inventors: Adam Heller; Ruben Maidan, both of Austin, Tex.

[73] Assignee: E. Heller & Company, Austin, Tex.

[21] Appl. No.: 753,812

[22] Filed: Sep. 3, 1991

Related U.S. Application Data

[63] Continuation-in-part of Ser. No. 664,054, Mar. 4, 1991.

[51] Int. Cl.$^5$ .................... C12Q 1/28; C12M 1/40; C07C 1/00; G01N 27/26
[52] U.S. Cl. ...................... 435/28; 435/288; 435/25; 435/291; 435/817; 435/26; 435/24; 435/14; 204/403; 204/153.1; 429/111; 429/40; 373/80
[58] Field of Search ................ 435/28, 25, 291, 817, 435/14, 24, 190, 26, 288; 429/111, 40; 373/80; 428/212; 204/157.15, 403

[56] References Cited

U.S. PATENT DOCUMENTS

| | | | |
|---|---|---|---|
| 4,098,574 | 7/1978 | Dappen | 435/14 |
| 4,168,205 | 9/1979 | Danninger et al. | 435/25 |
| 4,193,982 | 3/1980 | Avarmas et al. | |
| 4,224,125 | 9/1980 | Nakamura et al. | 435/817 |
| 4,247,297 | 1/1981 | Berti et al. | 435/24 |
| 4,356,074 | 10/1982 | Johnson | 435/190 |
| 4,375,399 | 3/1983 | Havas et al. | 435/14 |
| 4,390,621 | 6/1983 | Bauer | 435/14 |
| 4,404,066 | 9/1983 | Johnson | 435/817 |
| 4,418,148 | 11/1983 | Oberhardt | 435/14 |
| 4,427,770 | 1/1984 | Chen et al. | 435/14 |
| 4,461,691 | 7/1984 | Frank | 429/111 |
| 4,476,003 | 10/1984 | Frank et al. | 429/111 |
| 4,524,114 | 6/1985 | Samuels et al. | 429/40 |
| 4,545,382 | 10/1985 | Higgins et al. | 435/817 |
| 4,552,840 | 11/1985 | Riffer | 435/28 |
| 4,581,336 | 4/0886 | Malloy et al. | |
| 4,619,754 | 10/1986 | Niki et al. | 435/817 |
| 4,655,885 | 4/1987 | Hill et al. | 429/43 |
| 4,711,245 | 12/1987 | Higgins et al. | 435/817 |
| 4,717,673 | 1/1988 | Wrighton et al. | 373/80 |
| 4,721,601 | 1/1988 | Wrighton et al. | 429/213 |
| 4,758,323 | 7/1988 | Davis et al. | 435/26 |
| 4,764,416 | 8/1988 | Ueyama et al. | 428/212 |
| 4,776,944 | 10/1988 | Janata et al. | 435/817 |
| 4,784,736 | 11/1988 | Lonsdale et al. | 204/157.15 |
| 4,795,707 | 1/1989 | Niiyama et al. | 435/817 |
| 4,917,800 | 4/1990 | Lonsdale et al. | 204/157.15 |
| 4,919,767 | 4/1990 | Vadgama et al. | 435/817 |
| 4,927,516 | 5/1990 | Yamaguchi et al. | 435/817 |
| 4,938,860 | 7/1990 | Wogoman | 435/817 |
| 4,968,400 | 8/1988 | Ueyama et al. | 428/212 |

FOREIGN PATENT DOCUMENTS

| | | |
|---|---|---|
| 127958A2 | 5/1984 | European Pat. Off. |
| 125139 | 11/1984 | European Pat. Off. |
| 184909 | 6/1986 | European Pat. Off. |
| 241309 | 4/1987 | European Pat. Off. |
| 278647 | 8/1988 | European Pat. Off. |
| 368209A1 | 6/1989 | European Pat. Off. |
| 390390A1 | 3/1990 | European Pat. Off. |

OTHER PUBLICATIONS

Nagy, et al., "A New Type of Enzyme Electrode: The Ascorbic Acid Eliminator Electrode," Life Sciences, vol. 31, pp. 2611–2616, Pergamon Press, 1982.

Heller, A., "Electrical Wiring of Redox Enzymes," Reprinted from Accounts of Chemical Research, vol. 23, No. 5, 1990 (pp. 128–134).

Japanese Patent No. 03028752 A2 to Omochi, et al., "Method for Manufacture of an Electrode Containing Immobilized Enzyme and Interfering-Substance—Eliminating Membrane," (Abstract) Chemical Abstracts, 114(21):203143u.

(List continued on next page.)

Primary Examiner—Michael G. Wityshyn
Assistant Examiner—Louise N. Leary
Attorney, Agent, or Firm—Pravel, Hewitt, Kimball & Krieger

[57] ABSTRACT

A biosensor including an interferant-eliminating catalyst and method for analyzing an analyte in a biological sample is disclosed.

20 Claims, 3 Drawing Sheets

OTHER PUBLICATIONS

German Patent No. 3934299 C1, "Enzyme Electrodes Containing Oxidase and Peroxidase" to Schmid et al., (Abstract) Chemical Abstracts, 114(23):225208w.

Japanese Patent Application No. 02310457 A2, "Enzyme Biosensor For Micro Analysis of Body Fluid" (Abstract), Chemical Abstracts, 114(21):203111a.

Foulds, et al., "Immobilization of Glucose Oxidase in Ferrocene-Modified Pyrrole Polymers", Anal. Chem., vol. 60, No. 22, pp. 2473-2478 (1988).

Hale, et al., "A New Class of Amperometric Biosensor Incorporating a Polymeric Electron-Transfer Mediator," J. Am. Chem. Soc., vol. III, No. 9, pp. 3482-3484 (1989).

Foulds, et al., "Enzyme Entrapment in Electrically Conducting Polymers," J. Chem. Soc., Faraday Trans. 1, vol. 82, pp. 1259-1264 (1986).

Degani, et al., "Electrical Communication Between Redox Centers of Glucose Oxidase and Electrodes via Electrostatically and Covalently Bound Redox Polymers," J. Am. Chem. Soc., vol. III, pp. 2357-2358 (1989).

Bartlett, et al., "Strategies for the Development of Amperometri Enzyme Electrodes," Biosensors, vol. 3, pp. 359-379 (1987/1988).

Clark, et al., "Electrode Systems for Continuous Monitoring in Cardiovascular Surgery," Ann. N. Y. Acad. Sci., vol. 102, pp. 29-(1962).

Clark, et al., "Long-Term Stability of Electroenzymatic Glucose Sensors Implanted in Mice," Trans. Am. Soc. Artif. Inten. Organs, vol. 34, pp. 259-265 (1988).

Cass, et al., "Ferricinium Ion as an Electron Acceptor for Oxido-Reductases," J. Electroanal. Chem., vol. 190, pp. 117-127 (1985).

Alvery, et al., "Amperometric Enzyme Electrodes," Phil. Trans. R. Soc. Lond., vol. B 316, pp. 107-119 (1987).

Scheller, et al., "Enzyme Electrodes and Their Application," Phil. Trans. R. Soc. Lond., vol. B 316, pp. 85-94 (1987).

Pollak, et al., "Enzyme Immobilization by Condensation Copolymerization into Cross-Linked Polyacrylamide Gels," J. Am. Chem. Soc., vol. 102, No. 20, pp. 6324-6336 (1980).

Castner, et al., "Mass Transport and Reaction Kinetic Parameters Determined Electrochemically for Immobilized Glucose Oxidase," Biochemistry, vol. 23, No. 10, pp. 2203-2210 (1984).

Abstract of U.S. Pat. No. 4,193,982, Mar. 18, 1980, Avarmas, et al.

Abstract of Brandt, et al., "Covalent Attachment of Proteins to polysaccharide Carriers by Means of Benzoquinone," Biochim. Biophys. Acta, 386(1), 192-202 (1975).

Abstract of Narasihan, et al., "p-Benzoquinone Activation of Metal Oxide Electrodes for Attachment of Enzymes," Enzyme Microb. Technol., 7(6), 28-6 (1985).

Abstract of Ikeda, et al., "Glucose Oxidase-Immobilized Benzoquinone-carbon Past Electrode as a Glucose Sensor," Agric. Biol. Chem., 49(2), 541-3 (1985).

Abstract of U. Pat. No. 4,581,336, Apr. 8, 1986, Malloy, et al.

Abstract of European Patent No. 177,743 A2, Apr. 16, 1986.

Abstract of Bartlett, et al., "Modification of Glucose Oxidase by Tetrathiafulvalene," J. Chem. Soc., Chem. Commun., (16), 1135-6 (1990).

Yao, "Chemically-Modified Enzyme Membrane Electrode as an Amperometric Glucose Sensor," Analytica Chemica Acta, vol. 148, pp. 27-33 (1983).

Abstract of Albery, et al., "Amperometric Enzyme Electrodes, Part II. Conducting Salts as Electrode Materials for the Oxidation of Glucose Oxidase," J. Electroanal. Chem. Interfacial Electrochem., 194(2), 223-35.

Dicks, et al., "Ferrocene Modified Polypyrrole with Immobilised Glucose Oxidase and its Application in Amperometric Glucose Microbiosensors," Ann. Biol. Clin., vol. 47, pp. 607-619 (1989).

Yabuki, et al., "Electro-Conductive Enzyme Membrane," J. Chem. Soc., Chem. Commun., pp. 945-946 (1989).

Trojanowicz, et al., "Enzyme Entrapped Polypyrrole Modified Electrode for Flow-Injection Determination of Glucose," Biosensors & Bioelectronics, vol. 5, pp. 149-156 (1990).

Degani, Y. and Heller, A., "Direct Electrical Communication Between Chemically Modified Enzymes and Metal Electrodes. 1. Electron Transfer from Glucose (List continued on next page.)

OTHER PUBLICATIONS

Oxidase to Metal Electrodes via Electron Relays, Bound Covalently to the Enzyme," Journal of Physical Chemistry, vol. 91, pp. 1285–1289 (1987).

Degani, Y. and Heller, A., "Direct Electrical Communication Between Chemically Modified Enzymes and Metal Electrodes. 2. Methods for Bonding Electron-Transfers Relays to Glucose Oxidase and D-Amino-Acid Oxidase," JACS, vol. 110, pp. 2615–2620 (1988).

Bartlett, et al., "Covalent Binding of Electron Relays to Glucose Oxidase," J. Chem. Soc., Chem. Commun., pp. 1693–1704.

Umana, U.S. Army Research Office Report No. ARO 23106.3-LS entitled "Protein-Modified Electrochemically Active Biomaterial Surface," dated Dec. 1988.

Samuels, et al., "An Electrode-Supported Oxidation Catalyst Based on Ruthenium (IV). pH 'Encapsulation' in a Polymer Film," J. Am. Chem. Soc., vol. 103, pp. 307–312 (1981).

Denisevich et al., "Unidirectional Current Flow and Charge State Trapping at Redox Polymer Interfaces on Bilayer Electrodes: Principles, Experimental Demonstration, and Theory," J. Am. Chem. Soc., vol. 103, pp. 4727–4737 (1981).

Abruna, et al., "Rectifying Interfaces Using Two-Layer Films of Electrochemically Polymerized Vinylpyridine and Vinylbipyridine Complexes of Ruthenium and Iron on Electrodes," J. Am. Chem. Soc., vol. 103, pp. 1–5 (1981).

Ellis, et al., "Selectivity and Directed Charge Transfer Through an Electroactive Metallopolymer Film," J. Am. Chem. Soc., vol. 103, pp. 7480–7483 (1981).

INTERFERANT ELIMINATING BIOSENSORS

This is a continuation-in-part application of pending U.S. application Ser. No. 07/664,054, filed Mar. 4, 1991.

FIELD OF THE INVENTION

This invention relates to biosensors, more particularly to an improved biosensor and method for detecting an analyte which minimizes or eliminates false signals caused by interfering substances in a biological sample.

BACKGROUND OF THE INVENTION

Amperometric biosensors are capable of quantifying trace amounts of biological analytes such as glucose, urea, cholesterol, etc. in biological fluids and foods. Analyte may be electrooxidized directly at the electrode, or an enzyme may be immobilized on an electrode such that the reaction product of the enzyme with its substrate is detected by an electrical change, e.g. change in current flow, at the electrode. The current generated at the electrode is a function of the quantity of analyte in a sample.

The accuracy of existing amperometric biosensors is compromised by the presence of additional electrooxidizable compounds (hereinafter termed "interferants") present in a biological test sample. Examples of such interferants include ascorbate, urate, bilirubin, cysteine and acetaminophenol.

It would be of great utility to provide a biosensor which would more accurately quantify an analyte without interference from other compounds present in a biological sample.

SUMMARY OF THE INVENTION

The present invention solves the prior art problems of interference by providing a biosensor having an interferant-eliminating layer. The interferant-eliminating layer includes a catalyst capable of oxidizing and thereby eliminating a plurality of interfering compounds before they reach the sensor. Consequently, the inventive interferant-eliminating biosensors permit the desired analyte to be more accurately quantified in a biological sample.

A biosensor of the present invention includes an electrode capable of specifically sensing an analyte to be detected and an interferant-eliminating layer containing a catalyst. The analyte may be sensed directly through electrooxidation on a metallic electrode or through sensing elements which are in electrical contact with the electrode, whereas the catalyst is isolated from electrical contact with the sensing elements and/or electrode. The electrical isolation of the catalyst from the electrode may be effected by means of an insulating barrier layer between the catalyst and electrode or sensing layer, or by selection of an operating potential for the bioassay at a level that prevents flow of current between the electrode and the catalyst.

In a preferred embodiment, a sensing layer contains a sensing enzyme. The sensing enzyme is preferably an oxidoreductase such as glucose oxidase for the detection of glucose, lactate oxidase for the detection of lactate, cholesterol oxidase for the detection of cholesterol, and the like. Preferred catalysts are horseradish peroxidase and iron (III) porphyrins such as hemin.

In an alternative preferred embodiment, the catalyst is "preactivated", or raised to a higher oxidation state, which eliminates the necessity for oxidant (e.g. hydrogen peroxide) to be present during bioassay. Preactivation of the catalyst is of particular utility in ex vivo applications, such as disposable biosensors and clinical analyzers.

DETAILED DESCRIPTION OF THE PREFERRED EMBODIMENTS

Figure 1:
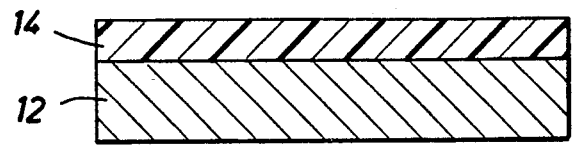
FIG. 1 is a schematic view of an electrochemical biosensor having a analyte sensing layer (layer I) on top of the electrode surface.

In its simplest embodiment, a biosensor of the present invention includes an electrode capable of specifically sensing an analyte to be detected, e.g., sensed directly by electrooxidation of analyte on a metallic electrode, and an interferant-eliminating layer.

Referring to FIGS. 1-3 and 6, a biosensor of the present invention may include an electrode 12 substantially covered by a sensing layer 14. The sensing layer contains a sensing enzyme and additional sensing elements required to achieve electrical contact with the electrode. The biosensor also includes an interferant-eliminating layer 16 containing a catalyst which is capable of oxidizing and thereby eliminating a plurality of interferants. The interferant-eliminating layer is isolated from electrical contact with the electrode, i.e., at a given applied potential at which components of the sensing layer are electrooxidized, or where analyte is directly electrooxidized on the electrode, the catalyst is not electroreduced.

In the case of "electrical contact", current will flow in the external circuit as a result of an oxidation or reduction reaction in one or more layers of the sensor. In the case of "electrical isolation", current in the external circuit will not flow as a result of an oxidation or reduction reaction in the isolated layer.

The electrode may be made of any material known for the manufacture of biosensing electrodes. Preferably, the electrode is formed of solid material, e.g. glassy carbon. Additional suitable electrode materials include graphite, platinum, palladium, tin oxide, and conducting organic salts. The electrode material itself may, in some cases, be able to directly sense and detect the analyte, for example, electrodes made of Group VIII metals or their oxides, such as palladium or ruthenium dioxide. Alternatively, a special sensing layer must be applied to the electrode material.

The analyte sensor or sensing layer may be the electrode itself or may be a film applied to the electrode which contains a specific enzyme which reacts with the analyte to be detected. It is intended that the term "sensing layer" include all the necessary sensing elements to provide electrical contact of the sensing enzyme with the electrode, permitting detection and transfer of a signal for analyzing an analyte. For example, this layer will include the specific sensing enzyme and also electron relays and/or diffusing redox mediators which participate in transporting electrons from enzyme to electrode. Any known method may be used to permit electrical contact between the sensing enzyme and the electrode. See, for example, U.S. Pat. No. 4,758,232 to Davis et al., which is hereby fully incorporated by reference.

Suitable sensing enzymes are oxidoreductases including dehydrogenases and oxidases. Examples of specific enzymes suitable for use are glucose oxidase for glucose analysis, lactate oxidase for lactate analysis, xanthine oxidase for xanthine analysis, cholesterol oxidase for cholesterol analysis, pyruvate oxidase for pyruvate analysis, L-amino acid oxidase for L-amino acid analysis, D-amino acid oxidase for D-amino acid analysis, alcohol oxidase for alcohol acid analysis, glycolate oxidase for glycolate analysis, sarcosine oxidase for sarcosine analysis, and other similar enzymes. In a preferred embodiment, glucose oxidase is used as the sensing enzyme in a biosensor for the measurement of glucose in a biological sample.

Mediators are electrochemically active fast redox couples that freely diffuse in solution. These include ions of conducting organic salts, quinones and their derivatives, organometallic complexes such as ferrocenes and their derivatives, and polypyridine complexes of transition metals such as osmium or ruthenium and their derivatives. Electron relays are enzyme or polymer-bound fast redox couples. A preferred group of electron relaying redox polymers is based on derivatives of a poly(vinylpyridine) complex of osmium bis (bipyridine) chloride. When the derivative is a polyamine, e.g., the backbone contains pyridinium-N-ethylamines, the redox polymer may be crosslinked using a crosslinking agent, such as poly(ethylene glycol)diglycidyl ether, to form a useful epoxy redox film.

The catalyst mediates oxidation of an interferant in the presence of an oxidant to yield a non-interfering compound which is no longer electrically active at the operating potential of the electrode and thus does not interfere with the biosensor's function. The catalyst may be a natural enzyme, e.g. horseradish peroxidase, or a synthetic catalyst such as an iron (III) porphyrin. Suitable catalysts include horseradish peroxidase, cytochrome c peroxidase, chloroperoxidase, lactoperoxidase, thyroid peroxidase, Japanese radish peroxidase a, Japanese radish peroxidase c, myeloperoxidase, NADH peroxidase, turnip peroxidase $A_1$, turnip peroxidase $A_2$, turnip peroxidase B, turnip peroxidase D, glutathione peroxidase, and transition metal porphyrins such as iron (III) porphyrins. A preferred iron (III) porphyrin is hemin, chloroprotoporphyrin IX iron (III). It is contemplated that additional, known metalloporphyrins may be useful as interferant-eliminating catalysts.

Horseradish peroxidase is a preferred catalyst because interferants present in biological fluids, such as ascorbate, urate, acetaminophen, bilirubin, and cysteine, are rapidly oxidized by hydrogen peroxide in the presence of horseradish peroxidase.

Hemin is a preferred catalyst for several reasons, including its high stability, and high specific activity per unit mass. These characteristics enable longer storage times and lower production costs. However, due to the smaller size and greater diffusivity of this catalyst, care must be taken to insure electrical isolation of the catalyst from the electron relays of the sensing layer. This isolation may be achieved by immobilizing and/or cross-linking the catalyst in a polymer matrix in a manner sufficient to prevent diffusion of the catalyst. An example of a suitable polymer for immobilization of hemin is poly-(N-vinylimidazole) (PVI). The imidazole moieties in this polymer coordinate to the iron center of the hemin, attaching it to the polymer matrix and increasing its activity. Additional imidazole containing polymers or copolymers or polymers containing other electron donating ligands may also be used to immobilize the catalyst.

The interferant-eliminating catalyst is isolated from electrical contact with the electrode. This isolation may be achieved by retaining the catalyst in a discrete layer surrounding the sensing layer. For example, a soluble catalyst in solution may be retained adjacent to the sensing layer within a dialysis membrane. Alternatively, a catalyst may be immobilized within a polymer or copolymer matrix. An immobilized catalyst may be further restricted by cross-linking to form an insoluble film, or by positioning a physical barrier between the sensing layer and the catalyst layer.

In a further embodiment, the desired electrical isolation may be achieved by selecting a catalyst which is not electroreduced at a potential where the analyte is electrooxidized. At a given applied potential, the electrode itself, the sensing elements, and catalyst may produce competing or non-competing oxidation and reduction currents. Therefore, appropriate selection of the catalyst, sensing elements and operating potential may be such that at the operating potential of a bioassay the catalyst, oxidizable by the oxidant, is not in electrical contact with the electrode, whereas the sensing enzyme, ususally reduced by the analyte, is in electrical contact with the electrode. That is, the operating potential is selected to maximize the direct or enzymatic electrooxidation of the substrate while minimizing direct or catalyst-mediated electroreduction of the oxidant or of the preactivated catalyst.

Figure 3:
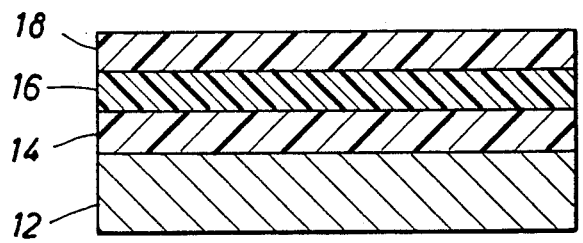
FIG. 3 is a schematic view of an electrochemical biosensor with an catalyst containing layer that eliminates interferants (layer II) and an oxidant generating layer (layer III) covering the catalyst containing layer.

The biosensor of the present invention minimizes or eliminates interference caused by reaction of other oxidizable compounds present in a test sample with the sensing elements. An interfering compound, upon reacting with the catalyst, is quickly oxidized by the oxidant and prevented from reaching the sensing element in its electrochemically active state. The oxidant, e.g. hydrogen peroxide, may be added to the assay solution or may be produced in situ by one or more oxidase enzymes, provided the corresponding enzyme substrates are present in the sample. These oxidase enzymes may be provided in a separate oxidant-generating layer or the oxidant-generating enzyme may be the same enzyme as that used as the sensing enzyme. For example, in a glucose biosensor, glucose oxidase can both mediate the oxidation of glucose, permitting the analysis of glucose through electron relays coupled to the electrode and also mediate the oxidation of glucose by oxygen, generating hydrogen peroxide which may be subsequently used with the catalyst for eliminating interferants. However, it is generally preferred that an oxidant-generating enzyme be mixed with or located in close proximity to the interferant eliminating catalyst, e.g., in an adjacent layer, as shown in FIG. 3.

In a preferred embodiment, the catalyst is "preactivated", thereby eliminating the requirement for oxidant present in the sample or an oxidant-generating system. The preactivated catalyst also reduces the necessity of a multi-layer system, in an interferant-eliminating biosensor.

Preactivation includes the preoxidation of the catalyst by an oxidant, e.g. hydrogen peroxide, to form a stable, oxidized catalyst intermediate. The preactivated catalyst thus has one or more centers with a higher oxidation state. At the time of assay, and in the presence of interferants, the catalyst will be regenerated and interferants oxidized.

A biosensor having a preactivated catalyst obviates the need for diffusing oxidant to be present during the biochemical analysis or for the biosensor to include an oxidant generating enzyme. A preactivated biosensor allows the reaction with interferants to proceed rapidly until the catalyst in its reactive, oxidized form is exhausted. When the oxidized catalyst is exhausted, it may be regenerated, e.g., by brief exposure to an oxidant.

The availability of a biosensor containing a preactivated catalyst allows the prompt use of oxidizing equivalents in the preactivated catalyst immediately when the analyte measurements begin. As discussed further in Example 6, this permits a time window between the start of analyte measurement and the onset of the interferant signal, allowing completion of the measurement of the analyte prior to the onset of the interferant signal.

Figure 2:
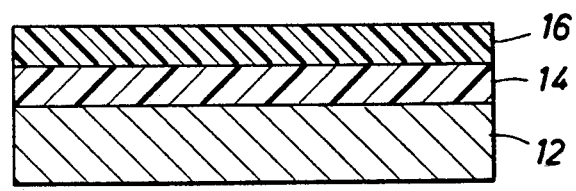
FIG. 2 is a schematic view of an electrochemical biosensor with a catalyst-containing layer (layer II) that eliminates interferants.
Figure 6:
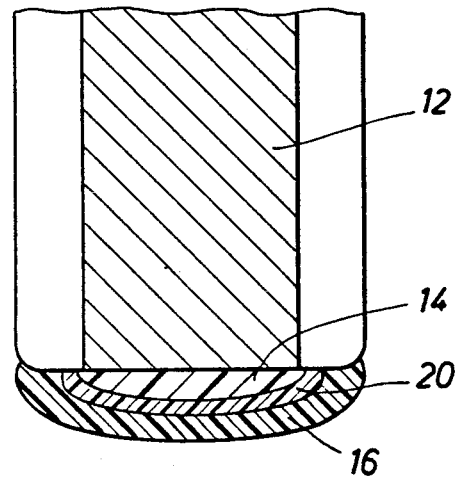
FIG. 6 is a schematic diagram of a multilayer electrode having a barrier layer between the catalyst containing layer and the analyte sensing layer.

As shown in FIGS. 1–3, biosensors of the present invention may be multi-layered. An electrode 12 is substantially covered by a sensing layer (layer I) 14 containing sensing elements in electrical contact with the electrode. An interferant-eliminating, catalyst-containing layer (layer II) 16 may be adjacent to the sensing layer 14, or may be physically separated from the sensing elements by a barrier layer 20 as shown in FIG. 6. An oxidant-generating layer 18 (layer III) may be adjacent to the catalyst layer 16. Electrical isolation of the catalyst from the electron relays of the sensing layer can be achieved by physical separation, e.g., by physical barriers, immobilization of elements within a matrix, and/or matrix crosslinking. Electrical isolation of the catalyst from diffusional redox mediators can be effected through an ion exchange membrane. For example, an anionic diffusional redox mediator will be retarded by a polyanionic cation exchange membrane. Likewise, a cationic diffusional redox mediator will be retarded by a polycationic ion exchange membrane.

Alternatively, and as discussed above, electrical isolation may be achieved by selecting the components of the biosensor and the operating potential to maximize the response of the sensing enzyme while minimizing competing responses. In this embodiment, the catalyst and sensing elements need not be provided in distinct layers.

In the method of the present invention, the inventive biosensor is used as a working electrode to detect and quantify the amount of an analyte in a biological sample. These biosensors may be used in known electrochemical sensing methods, including amperometric, coulometric, potentiometric, conductometric or impedimetric methods. A preferred use is in amperometric methods.

For example, in an amperometric method, a sample is placed in a three-electrode glass cell containing an electrolyte and working, reference, and counter electrodes. A saturated calomel electrode may be the reference electrode. An electrochemical potential is applied to the working electrode with respect to the reference electrode and current flow is measured as a function of time. The potential applied will depend on the redox potential of the mediator or the relay of the sensing elements. The measured current is a function of the concentration of the substances being oxidized. When the catalyst is not active, both analyte and interferants are oxidized, and the measured current reflects the combined concentration of analyte and interferants, resulting in inaccurate analyte measurements. When the catalyst is active, interferants are oxidized and do not reach the analyte sensing electrode or the elements of the analyte sensing layer in electrical contact with the electrode. The measured current then more correctly reflects only the concentration of the analyte.

Under certain operating conditions the catalyst, coupled with the electron relays present in the analyte sensing layer, may enhance the rate of electrochemical reduction of the oxidant. This process may result in a reduction current superimposed on the oxidation current of the analyte and the net current will no longer be proportional to the analyte concentration. This undesirable situation may be prevented by making the potential of the working electrode sufficiently oxidizing such that reduction process will not proceed at a substantial rate, whereas analyte electrooxidation will proceed rapidly. Alternatively, electrical contact between the catalyst and the sensing elements may be physically prevented.

A barrier layer, fabricated of a polymer film such as a cellulose derivative, polycarbonate, or perfluorinated membrane, may be used to effect such physical separation. Alternatively, the analyte sensing layer matrix may be crosslinked to make it less permeable to the catalyst. A protein crosslinked by a protein cross-linking agent such as glutaraldehyde or cyanuric chloride may be used.

In a further preferred embodiment, the catalyst is preactivated, i.e., brought to a higher oxidation state. The catalyst can be preactivated, for example, by reaction with an oxidant to create a relatively long-lived oxidized catalyst intermediate. Such preactivation obviates the necessity for oxidant to be present in the sample during the bioassay.

The following specific examples illustrate how the invention may be carried out but should not be considered as limiting the invention.

EXAMPLE 1

A piece of glassy carbon rod (10 mm long, 3 mm diameter, V 25 Vitreous Carbon, Atomergic Chemetals Corp., Farmington, N.Y.) was sealed in a glass tube with the insulating epoxy resin (Quick Stic—GC Electronics, Rockford, Ill.). A copper wire was attached to the rear end of the rod with electrically conducting silver epoxy (Epo-tek H20E, Epoxy Technology, Inc., Billerica, Mass.). The top end of the glass tube was polished with sand paper (grit 600) until a smooth surface was obtained, exposing a 3 mm disc of glassy carbon (the electrode surface). The electrode surface was pretreated by sequentially polishing with alumina powder (5.0, 1.0 and 0.3 micrometer particle size). After each polishing step the electrode surface was rinsed with deionized water, sonicated for 3 minutes and dried under a stream of nitrogen.

Synthesis of the Osmium Redox Polymer, ("POs-EA")

Cis-bis (2,2'-bipyridine-N,N') dichloroosmium (II) [Lay, P. A.; Sargeson, A. M.; Taube, H., *Inorg. Synth.*, Vol. 24, 1986, pp. 291–306] (0.494 g, 0.864 mmol) and poly(4-vinylpyridine) (PVP, Polysciences-Warrington, Pa., MW 50,000) (0.430 g, 4.09 milliequivalent) were heated under nitrogen at reflux in 18 ml ethylene glycol for 2 h. After cooling to room temperature, 30 ml dimethyl formamide and 1.5 g 2-bromoethylamine hydrobromide (7.3 millimole) were added and the solution was stirred at 45° C. overnight. The crude polymer was precipitated by pouring the solution into rapidly stirred acetone. The hygroscopic precipitate was collected, dissolved in $H_2O$, filtered, and precipitated as the $PF_6^-$ salt by addition of a solution of $NH_4PF_6$. The dry $PF_6^-$ salt (0.49 g) was then dissolved in 20 ml acetonitrile, diluted with 50 ml $H_2O$ and stirred over 5.2 g anion exchange beads (Bio-Rad AG1-X4, chloride form) for 2 hours. This solution was filtered, and then evaporated in vacuum to about 10 ml. Concentrated HCl was then added to bring the solution to pH 2, and the solution was dripped into rapidly stirred acetonitrile. The precipitate was filtered and dried in a vacuum desiccator.

Preparation of the analyte (glucose) sensing layer (layer I) comprised preparing a solution containing 2 mg/ml osmium redox polymer (POs-EA), 0.12 mg/ml polyethylene glycol diglycidyl ether (Polysciences MW 400), and 1 mg/ml glucose oxidase (Sigma type X, St. Louis, Mo., 128 units/mg) in a 5 mM HEPES buffer solution, pH 7.8. A one microliter droplet of the solution was applied to the electrode surface. The electrode was left in a vacuum desiccator at room temperature for 48 hours to set. The glucose sensing layer was further crosslinked by dipping the electrode in a 0.25% glutaraldehyde solution for 5 seconds, followed by rinsing with a phosphate buffer (pH 7.2, 0.1 molar (M) solution for 30 minutes. The purpose of this step is to avoid electrical contact between the electron relays in the glucose sensing layer and the peroxidase in the adjacent layer.

The catalyst containing layer (layer II) was prepared by depositing 5 microliters of a peroxidase (Sigma, type I, 85 units/mg) solution (100 mg/ml in a 0.1M phosphate buffer pH 7.2 containing 5 mg/ml glutaraldehyde) on top of the barrier layer and was left for two hours to set.

Electrochemical measurements were performed with a Princeton Applied Research Model 273 potentiostat/galvanostat and recorded on a x-y-t chart recorder. Measurements were performed in a three-electrode cell containing 5 ml of an electrolyte solution (0.1M phosphate buffer, pH 7.2 and 0.1M NaCl). The multilayer biosensor was used as the working electrode, a saturated calomel electrode (SCE) was used as the reference electrode, and a platinum wire was used as the counter electrode. The potential of the working electrode was held at 400 mV with respect to the SCE electrode and the current flowing was measured as a function of time. Five microliters of a stock solution of glucose or of the interferant were added to the electrolyte solution and rapidly mixed. Stock solutions of the interferant compounds (ascorbate, urate, bilirubin and acetaminophen) were freshly prepared because solutions of these compounds are unstable in air.

Figure 4A:
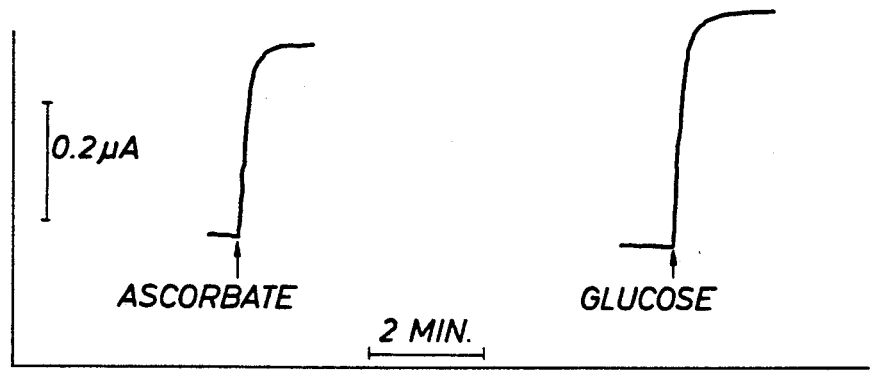
FIG. 4 shows the results of a measurement performed with an electrode of the type described in Example 1. The signals (current as a function of time) obtained upon additions of ascorbate (0.1 mM) and glucose (2 mM) are shown in the absence of hydrogen peroxide (a), and shown in the presence of hydrogen peroxide (b) (0.1 mM).
Figure 4B:
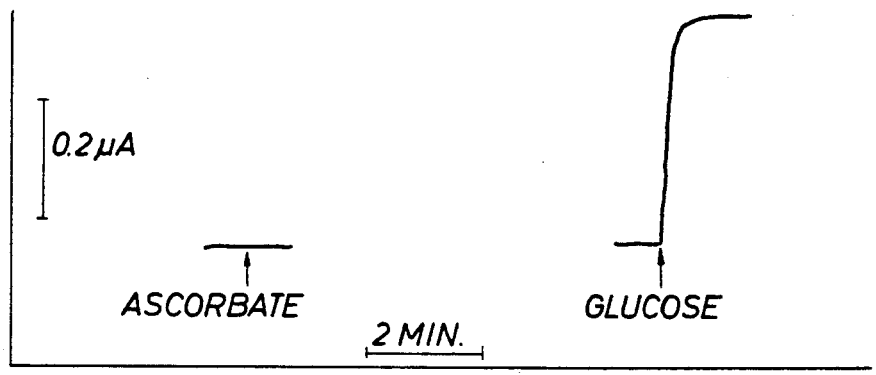

FIG. 4 shows the results of an experiment using a sensor as described above. In this experiment, glucose (final concentration 2.0 mM) and ascorbate (final concentration 0.1 mM) were separately added and mixed rapidly. FIG. 4(a) shows the currents measured in the absence of hydrogen peroxide. FIG. 4(b) shows the currents measured in the presence of hydrogen peroxide (0.1 mM).

Figure 5A:
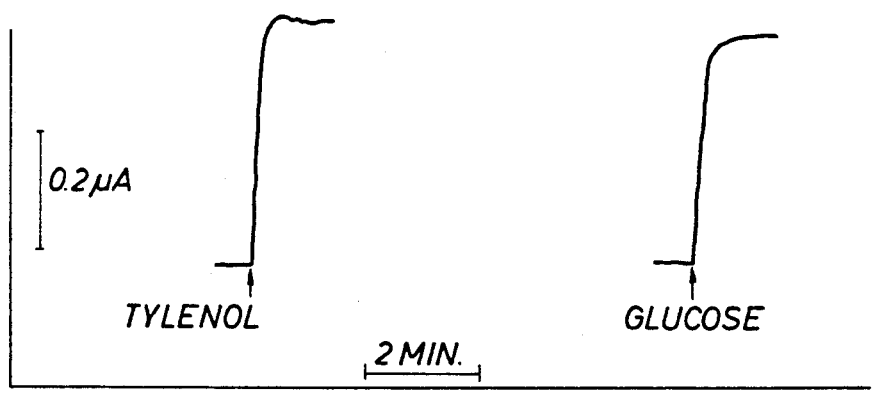
FIG. 5 shows the results of a measurement performed with an electrode of the type described in Example 1. The signals (current as a function of time) obtained upon additions of acetaminophen (0.1 mM) and glucose (2 mM) are shown in the absence of hydrogen peroxide (a), and in the presence of hydrogen peroxide (0.1 mM) (b).
Figure 5B:
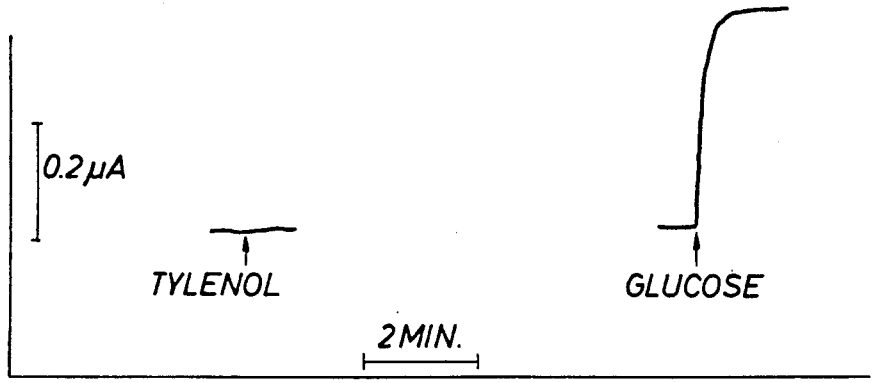

FIG. 5 shows the results of a similar experiment with different interferants. In this experiment, glucose (final concentration 2.0 mM) and acetaminophen (final concentration 0.1 mM) were separately added and mixed rapidly. FIG. 5(a) shows the currents in the absence of hydrogen peroxide. FIG. 5(b) shows the currents measured in the presence of hydrogen peroxide (0.1 mM).

As shown in FIGS. 4 and 5, when $H_2O_2$ is present the false signal from the interferant is substantially reduced. The glucose signal is not affected by the catalyst containing layer that eliminates the interferants. Similar results are obtained when uric acid or bilirubin are the interferants instead of ascorbate or acetaminophen. Similar results are also obtained when a mixture of interferants is present. It is anticipated that similar results will be obtained from other interferants (such as cysteine) that are oxidized by hydrogen peroxide in the presence of the catalyst (e.g. peroxidase) containing layer. The results shown in FIGS. 4 and 5 are for experiments done with separately added glucose and interferant. When a mixture containing glucose and one or more of the interferants is injected in the presence of $H_2O_2$ the current measured is equivalent to that measured for the injection of glucose alone. This indicates that the interferant eliminating catalyst layer works as expected and prevents multiple interferants from reaching the electroactive layer.

The biosensor described in Example 1 is an embodiment appropriate for use where hydrogen peroxide may be added to the analyte test solution from an external source. Examples of applications of this method include use for clinical analysis of samples (ex vivo), or analysis of samples in industrial processes, such as in food and beverage preparation. This biosensor is particularly appropriate in flow injection analysis where a pulse of an oxidant solution can preceed a pulse of the analyte solution.

EXAMPLE 2

An electrode was prepared as described in Example 1. On top of the catalyst containing layer a hydrogen peroxide generating layer containing lactate oxidase (LOD) was immobilized by crosslinking it with glutaraldehyde (FIG. 3). This layer was prepared by depositing 5 microliters of LOD (Finnsugar, Schaumburg, Ill., 33 units/mg) solution (100/mg/ml in a 0.1M phosphate buffer pH 7.2 containing 5 mg/ml glutaraldehyde) on the catalyst layer. The sensor was then left for two hours to set.

The experimental use of this electrode was similar to that described in Example 1 except that the oxidant was generated from lactate and molecular oxygen. Thus, hydrogen peroxide was not added to the analyte solution. The results obtained with this electrode were similar to the results described in Example 1.

The biosensor described in Example 2 is preferred when it is undesirable to add hydrogen peroxide to the analyte test solution from an external source. Examples of such cases include in vivo measurements, disposable sensors for analysis of small amounts of analyte solution (for example, blood drops), or industrial fermenters or reactors.

EXAMPLE 3

An electrode was prepared as described in Example 1 for the electrode surface pretreatment and analyte sensing layer preparation. This layer was not further crosslinked with glutaraldehyde nor was it coated with a barrier layer. The catalyst containing layer was coated directly on top of the analyte sensing layer by immobilizing peroxidase on a hydrazide polymer matrix. Specifically, the catalyst containing layer was immobilized as follows: Solution (A) comprised 5 mg/ml polyacrylamide hydrazide (Water soluble, Sigma #P9905) dissolved in water. Solution (B) comprised 2 mg peroxidase (Sigma, type VI, 260 units/mg) dissolved in 100 microliters 0.1M sodium bicarbonate solution. Sodium periodate (50 microliter of a 12 mg/ml solution) was added to solution (B) and that solution was incubated in the dark at room temperature (20°–25° C.) for 2 hours.

After the incubation, 7.5 microliter from Solution (A) were added to Solution (B) and 10 microliter of the mixture were applied on top of the glucose sensing layer. The electrode was left to set for 2 hours and then used. In an alternative method, the crosslinked film could be formed without the polyacrylamide hydrazide polymer.

It is understood that the above-described method using Solutions (A) and (B) are interchangeable with similar procedures using glutaraldehyde (or similar compounds), and vice versa. The method using Solutions (A) and (B) tends to be milder than other methods because it tends to destroy less of compounds it contacts.

This electrode was used in a manner similar to that described for Example 1 except that a more oxidizing potential (500 mV v. SCE instead of 400 mV vs. SCE) was applied to the working electrode. The results obtained with this electrode were similar to the results described in Example 1.

An advantage of this biosensor structure is that it is simpler, having one less layer than the biosensor of Example 1 (i.e., does not entail application of an intermediate layer between the analyte sensing layer and the catalyst containing layer).

The elimination of interferants described in these three examples is also beneficial in that such elimination improves the stability of the sensor, the sensing layer of which may be degraded by reaction with intermediates generated by the oxidation of interferants. Specifically, the catalytic oxidation of urate ions improves the long term stability of the sensors.

EXAMPLE 4

Poly-(N-vinylimidazole) (PVI) [prepared by the method of Chapiro et al., Eur. Polym. J., 24: 1019–1028 (1988)] was dissolved in water (10 mg/ml). Hemin (bovine, #85,856-0 Aldrich, Milwaukee, Wis.) was dissolved in a water/ethanol (25/75 by volume) solution containing NaOH (0.01M). The concentration of the hemin in this solution was 5 mg/ml.

A crosslinked hemin-containing gel was prepared by one of the two following methods and cured directly on the surface of a polished glassy carbon electrode similar to the one described in Example 1:

1) A PVI gel was prepared using as a diepoxide crosslinker polyethyleneglycol diglycidyl ether (PEGDGE), average molecular weight 400 (#08210 Polysciences Inc., Warrington, Pa.) (2 mg/ml solution in water). Ten microliters of PVI solution were mixed with 2 $\mu$l of PEGDGE solution and coated on top of the electrode. After curing for 24 hours the crosslinked gel was dipped into the hemin solution for 5 minutes and then rinsed with water. In this step, hemin was complexed into the PVI matrix, binding to the imidazole groups of the polymer.

2) A gel was prepared by a one step procedure using the hemin as the crosslinker. Ten microliters of PVI solution were mixed with 10 $\mu$l of hemin solution, applied on top of the electrode, and allowed to dry for 2 hours. The resulting film was no longer water soluble and contained the hemin necessary as catalyst for interferant elimination.

Figure 7:
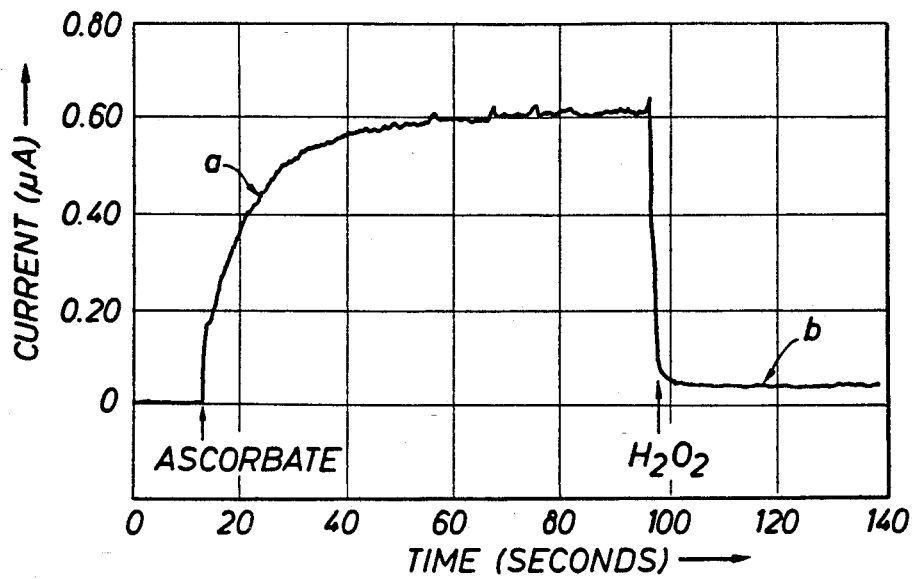
FIG. 7 shows the results of measurements performed with the hemin-containing electrode of Example 4. The signals (current as a function of time) obtained upon additions of ascorbate (0.1 mM) are shown in the absence of hydrogen peroxide (a), and are shown in the presence of hydrogen peroxide (b) (1.0 mM).

FIG. 7 shows the results obtained with a glassy carbon electrode that was directly coated with hemin by the first method. The experimental measurement conditions were similar to those described in Example 1. It can be seen that injection of ascorbate resulted in an oxidation current. When hydrogen peroxide was added to the solution, the current decreased indicating elimination of the ascorbate due to its PVI-hemin catalyzed oxidation by $H_2O_2$.

EXAMPLE 5

The basis of the delayed elimination of interferants is demonstrated using an electrode produced as described for Example 3. The experimental set-up was similar to that described for Example 1.

Figure 8:
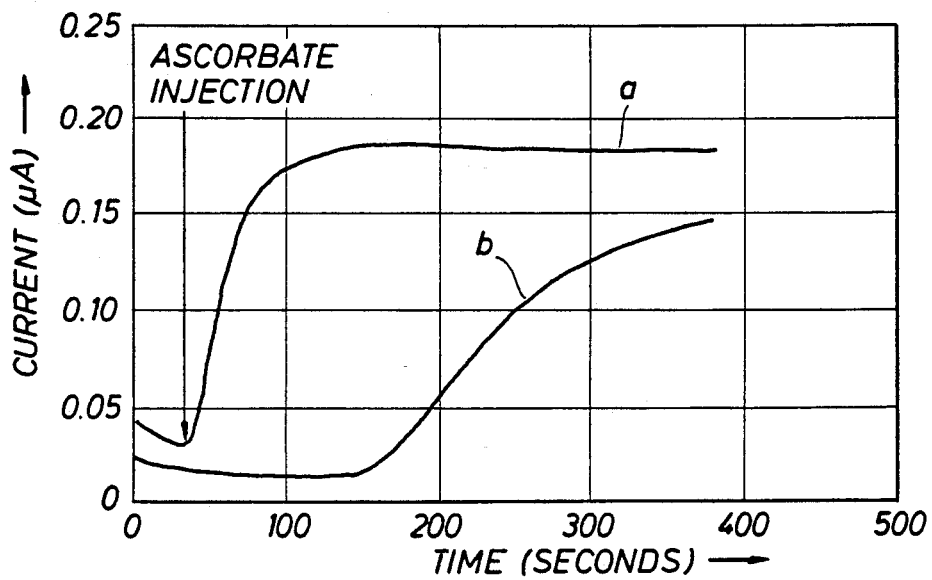
FIG. 8 shows the results of experiments comparing the response of a preactivated biosensor of Example 5 with that of a non-preactivated biosensor. The signals (current as a function of time) obtained are shown for a non-preactivated biosensor (a) and a preactivated biosensor (b).

Ascorbate (final concentration 0.1 mM) was injected into the cell and rapidly mixed to achieve an homogeneous solution. As shown in FIG. 8, when the electrode was not preactivated, injection of ascorbate resulted in a rapid rise in the oxidation current (false signal). When the same electrode was preactivated by its exposure to 0.2 mM $H_2O_2$ for 10 seconds followed by rinsing with the buffer solution, injection of ascorbate resulted in no response for over 100 seconds whereafter the rise of the oxidation current remained slow.

EXAMPLE 6

All experiments in this example were conducted in a petri dish electrochemical cell (35 mm diameter × 10 mm height). The working electrode was a glassy carbon (vitreous carbon) rotating-disk electrode (3 mm diameter) encapsulated in a teflon rod (12 mm diameter), mounted on a Pine Instruments (Grove City, Pa.) AFMSRX electrode rotator. A standard calomel electrode was the reference electrode and a platinum wire was the counter electrode. The electrolyte solution (5 ml) contained phosphate buffer (pH 7.2, 0.1M) and NaCl (0.1.M). A model 273 potentionstat/galvanostat (EG & G Princeton Applied Research) using the model 270 electrochemical analysis system software was used throughout the experiments.

The electrodes were assembled in a fixed position while the petri dish was mounted on an adjustable base that allowed to change its position with respect to the electrodes. There were two possible positions: (1) when the cell was raised the electrodes were immersed into the cell solution, (2) when the cell was lowered the electrodes were no longer in contact with the solution and were exposed to the air.

Prior to the beginning of each measurement the cell was lowered and the electrodes rinsed three times with buffer solution and dried by blowing air and rotating the working electrode at 2500 RPM for 10 seconds to expel any remaining buffer. Measurement was initiated by rising the petri dish in such a way that the three electrodes were submerged into the analyte solution and immediately applying the working potential while measuring the resulting current for several minutes. Between measurements the petri dish was lowered exposing the electrodes that were again washed and dried in the above described fashion. At this point the electrode was exposed to the oxidant for preactivation, washed and dried again.

Figure 9:
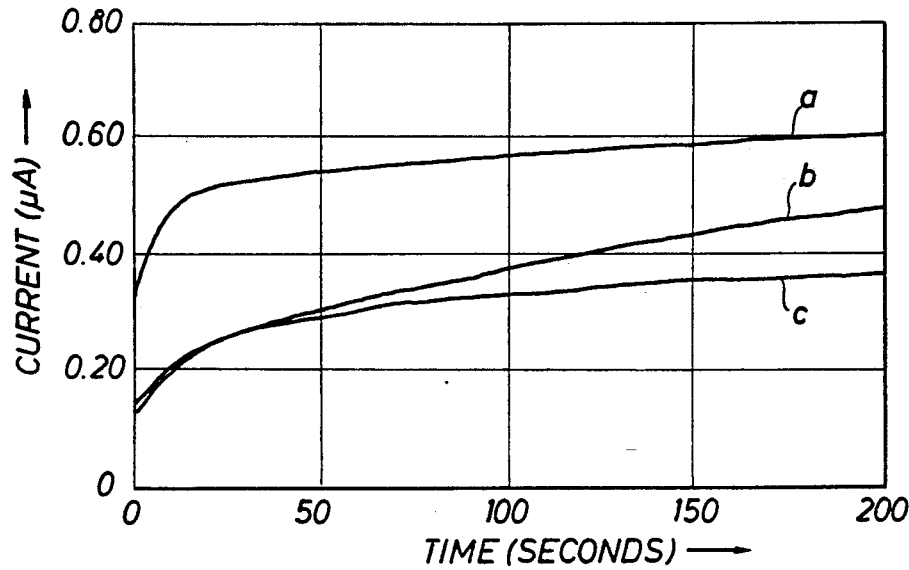
FIG. 9 shows the results of experiments comparing the preactivated biosensor of Example 6 with a non-preactivated biosensor in measuring glucose in the presence of an interferant. The signals (current as a function of time) are shown for a non-preactivated biosensor (a) and a preactivated biosensor (b). A control signal obtained in the absence of interferants is also shown (c).

FIG. 9 shows the results of experiments carried out by the above-described manner with a working electrode prepared in a similar way to that described in Example 3. In the first experiment, the electrode was not preactivated and after rinsing and drying the electrode, the cell containing 0.5 mM ascorbate and 5.0 mM glucose was raised. A potential of 400 mV vs SCE was applied to the working electrode and as a result a rapid rise in oxidation current [curve (a)] was observed. When the same experiment was repeated after the working electrode had been preactivated by exposure to $H_2O_2$ (0.2 mM), curve (b) was obtained. A control experiment was performed with a cell that did not contain ascorbate but only glucose (5.0 mM). The glucose-only control experiment is shown in curve (c). In this case, the currents were the same for the preactivated and the non-preactivated electrode.

These results are explained by the elimination of ascorbate in curve (b). For up to 50 seconds from the start of the measurement, the current measured with the preactivated electrode (b) in the presence of glucose and interferant is similar to that measured when only glucose is present (c). Only after this period, in which centers oxidized in the preactivation step are exhausted, did the current in curve (b) start increasing to eventually attain the level of curve (a). These experiments show that for the preactivated electrode the current measured before the onset of the interferant ascorbate oxidation (50 seconds in this case) is solely a function of to the glucose concentration and is not be affected by the presence of ascorbate.

Although the invention has been described with reference to its preferred embodiments, those of ordinary skill in the art may, upon reading this disclosure, appreciate changes and modifications which do not depart from the scope and spirit of the invention as described above or claimed hereafter.

We claim:

1. A biosensor comprising:
   an electrode on which an analyte is electrooxidized at a given applied potential; and
   an interferant-eliminating layer substantially covering the electrode but electrically isolated therefrom at the given applied potential, comprising a catalyst which is capable of catalyzing substantial oxidation of a plurality of interferants but not substantial oxidation of the analyte.

2. A biosensor comprising:
   an electrode on which an analyte is electrooxidized at a given applied potential; and
   an interferant-eliminating layer substantially covering the electrode but electrically isolated therefrom, comprising a preactivated, oxidized catalyst which is capable of catalyzing substantial oxidation of a plurality of interferants but not substantial oxidation of the analyte.

3. The biosensor of claim 2, further comprising a sensing layer in which analyte is electrooxidized, said sensing layer substantially covering and in electrical contact with the electrode.

4. The biosensor of claim 3, wherein the sensing layer includes a sensing enzyme which catalyzes oxidation of analyte.

5. The biosensor of claim 4, wherein the sensing enzyme is an oxidoreductase.

6. The biosensor of claim 5, wherein said oxidoreductase is glucose oxidase, lactate oxidase, xanthine oxidase, cholesterol oxidase, pyruvate oxidase, L-amino acid oxidase, D-amino acid oxidase, alcohol oxidase, urate oxidase, aldehyde oxidase, glycolate oxidase, or sarcosine oxidase.

7. The biosensor of claim 6, wherein said oxidoreductase is glucose oxidase.

8. The biosensor of claim 2, wherein the preactivated catalyst is insulated from electrical contact with the electrode by a physical barrier.

9. The biosensor of claim 8, wherein the physical barrier is a membrane.

10. The biosensor of claim 9, wherein the membrane is an ion exchange membrane.

11. The biosensor of claim 5, wherein relative redox potentials at the sensing layer and at the interferant-eliminating layer are such that at the given applied potential, the oxidoreductase is in electrical contact with the electrode and the interferant-eliminating layer is electrically isolated from the electrode.

12. The biosensor of claim 2, wherein said catalyst is horseradish peroxidase, cytochrome c peroxidase, chloroperoxidase, lactoperoxidase, thyroid peroxidase, Japanese radish peroxidase a, Japanese radish peroxidase c, myeloperoxidase, NADH peroxidase, turnip peroxidase $A_1$, turnip peroxidase $A_2$, turnip peroxidase B, turnip peroxidase D, glutathione peroxidase, or a transition metal porphyrin.

13. The biosensor of claim 12, wherein said catalyst is horseradish peroxidase.

14. The biosensor of claim 12, wherein said catalyst is an iron (III) porphyrin.

15. The biosensor of claim 14, wherein said iron (III) porphyrin is hemin.

16. A process for producing a preactivated interferant-eliminating biosensor, said process comprising the steps of:

substantially covering an electrode on which an analyte is electrooxidized with an interferant-eliminating layer comprising a catalyst, said catalyst capable of catalyzing substantial oxidation of a plurality of interferants but not substantial oxidation of the analyte; and reacting the catalyst with an oxidant to substantially increase the oxidation state of the catalyst and to form a stable, oxidized catalyst intermediate.

17. A process for producing a preactivated, interferant-eliminating biosensor, said process comprising the steps of:

substantially covering an enzyme electrode on which an analyte is electrooxidized with an interferant-eliminating layer containing a catalyst, said catalyst capable of catalyzing substantial oxidation of a plurality of interferants but not substantial oxidation of the analyte;

reacting the catalyst with an oxidant to increase the oxidation state of the catalyst and to form a stable, oxidized catalyst intermediate.

18. A process for analyzing analyte in the presence of a plurality of interferants in a test sample comprising the steps of:

contacting a sample with a preactivated, interferant eliminating biosensor having an electrode and an interferant eliminating layer;

substantially oxidizing interferants in the interferant eliminating layer; and detecting the analyte at the electrode in the absence of substantial interference.

19. The process of claim 18, wherein said contacting is in the absence of oxidant in the sample.

20. The process of claim 18, wherein said analyte is glucose, lactate, xanthine, cholesterol, pyruvate, an L- or D-amino acid, alcohol, glycolate, or sarcosine.

* * * * *